United States Patent
Biggel et al.

(10) Patent No.: US 9,487,316 B2
(45) Date of Patent: Nov. 8, 2016

(54) METHOD AND APPARATUS FOR SEPARATING AND STACKING SLICES OF FOOD

(71) Applicant: Hochland SE, Heimenkirch (DE)

(72) Inventors: Andreas Biggel, Hergatz (DE); Tobias Schellheimer, Wangen (DE)

(73) Assignee: HOCHLAND SE, Heimenkirch ( * ) Notice: Subject to any disclaimer, the term of this patent is extended or adjusted under 35 U.S.C. 154(b) by 58 days.

(21) Appl. No.: 14/375,724

(22) PCT Filed: Jan. 31, 2013

(86) PCT No.: PCT/EP2013/051929
§ 371 (c)(1),
(2) Date: Jul. 30, 2014

(87) PCT Pub. No.: WO2013/113828
PCT Pub. Date: Aug. 8, 2013

(65) Prior Publication Data
US 2015/0044010 A1 Feb. 12, 2015

(30) Foreign Application Priority Data

Feb. 1, 2012 (DE) .................. 10 2012 001 831

(51) Int. Cl.
*B26D 7/06* (2006.01)
*B65B 35/50* (2006.01)
(Continued)

(52) U.S. Cl.
CPC .............. *B65B 35/50* (2013.01); *A01J 27/00* (2013.01); *A23C 19/0908* (2013.01);
(Continued)

(58) Field of Classification Search
CPC ............ B65H 2406/3452; B65H 2406/34525; B65H 39/14; B65B 35/46; Y10T 156/1052
USPC ........ 156/250, 256, 259, 269, 270; 198/418, 198/441, 450, 456, 458, 471.1; 271/178; 414/793.9
See application file for complete search history.

(56) References Cited

U.S. PATENT DOCUMENTS 3,458,059 A    7/1969 Olsen
3,580,442 A *  5/1971 Rohdin .................. B65B 43/46
                                                 198/458

(Continued)

FOREIGN PATENT DOCUMENTS

DE   297 13 690 U1     1/1999
IT   WO 03016184 A2 *  2/2003 ............. B65H 29/54

(Continued)

*Primary Examiner* — Gregory Adams
(74) *Attorney, Agent, or Firm* — Stolmar & Partner; Robert Lelkes

(57) ABSTRACT

Disclosed is a method for separating and stacking slices of food, in particular slices of cheese (2). In said method, a plurality of slices of food (2) is continuously conveyed by a feeding belt conveyor (3) such that the slices of food adjoin each other in rows. A rotating transfer roll (5) picks up the slices of food (2) from the feeding belt conveyor (3) and places same on top of each other in a stacking zone (4), the transfer roll (5) jointly accommodating a row of slices of food by means of a corresponding plurality of holding units (6). During rotation of the transfer roll, the individual slices of food (2) are separated from each other as a result of a relative movement of the holding units in the axial direction, and the separated individual slices (2) detach from the holding units (6) and are stacked on top of each other in the stacking zone (4).

9 Claims, 2 Drawing Sheets

(51) Int. Cl.
  *A61F 13/15* (2006.01)
  *A01J 27/00* (2006.01)
  *A23C 19/09* (2006.01)
  *B65H 29/32* (2006.01)
  *B65H 29/40* (2006.01)

(52) U.S. Cl.
  CPC .. *A61F 13/15756* (2013.01); *A61F 13/15764* (2013.01); *B26D 7/06* (2013.01); *B65H 29/32* (2013.01); *B65H 29/40* (2013.01)

(56) References Cited

U.S. PATENT DOCUMENTS

| | | | | |
|---|---|---|---|---|
| 4,200,179 A | * | 4/1980 | Hinz | A24C 5/478 198/458 |
| 4,523,671 A | * | 6/1985 | Campbell | B65G 47/71 198/429 |
| 4,538,629 A | * | 9/1985 | Grasse | A24C 5/333 131/282 |
| 4,676,360 A | * | 6/1987 | Mattei | A24C 5/336 198/377.1 |
| 4,921,235 A | | 5/1990 | Biagiotti | |
| 5,149,554 A | | 9/1992 | Abler | |
| 6,170,636 B1 | * | 1/2001 | Een | A61F 13/15666 198/441 |
| 6,832,679 B2 | * | 12/2004 | Berndtsson | G06K 13/08 198/471.1 |
| 7,255,219 B2 | * | 8/2007 | Rinke | A24C 5/478 131/282 |
| 7,334,674 B2 | * | 2/2008 | Berndtsson | B65C 9/42 198/471.1 |
| 7,540,369 B2 | * | 6/2009 | Momich | B65B 35/46 198/418 |
| 7,837,025 B2 | * | 11/2010 | Draghetti | A24C 5/478 131/94 |
| 8,790,232 B2 | | 7/2014 | Pastrello | |
| 2004/0159246 A1 | | 8/2004 | Weber | |
| 2008/0276439 A1 | * | 11/2008 | Andrews | A61F 13/15577 29/428 |
| 2009/0183970 A1 | * | 7/2009 | Ramminger | B65G 47/71 198/471.1 |
| 2010/0158658 A1 | * | 6/2010 | Konstandin | A61F 13/15601 414/752.1 |
| 2010/0192739 A1 | * | 8/2010 | Piantoni | A61F 13/15756 83/26 |
| 2013/0291483 A1 | | 11/2013 | Van Gerwen | |

FOREIGN PATENT DOCUMENTS

| | | |
|---|---|---|
| JP | 2009-143677 A | 7/2009 |
| WO | 2007/122311 A1 | 11/2007 |

* cited by examiner

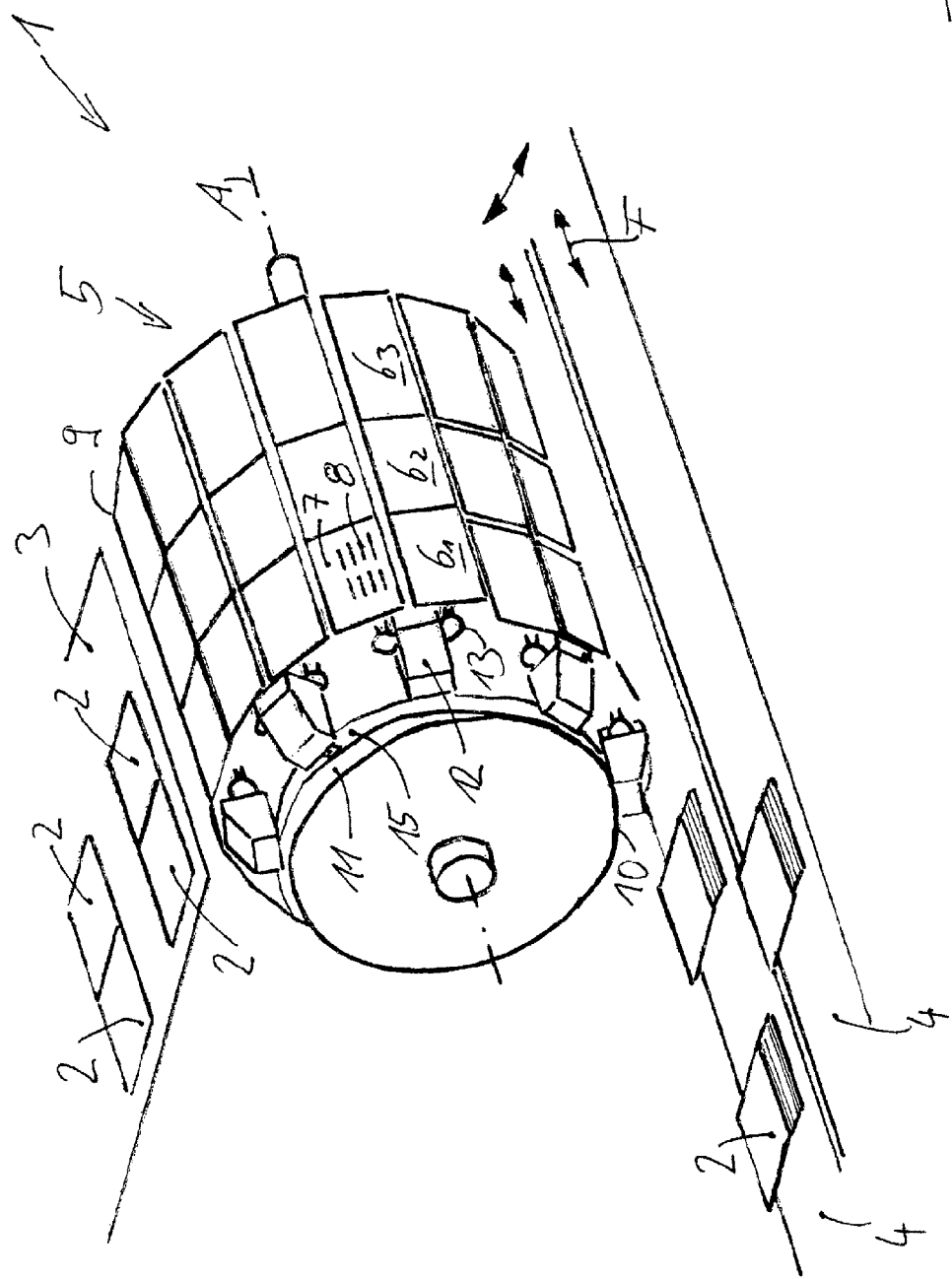

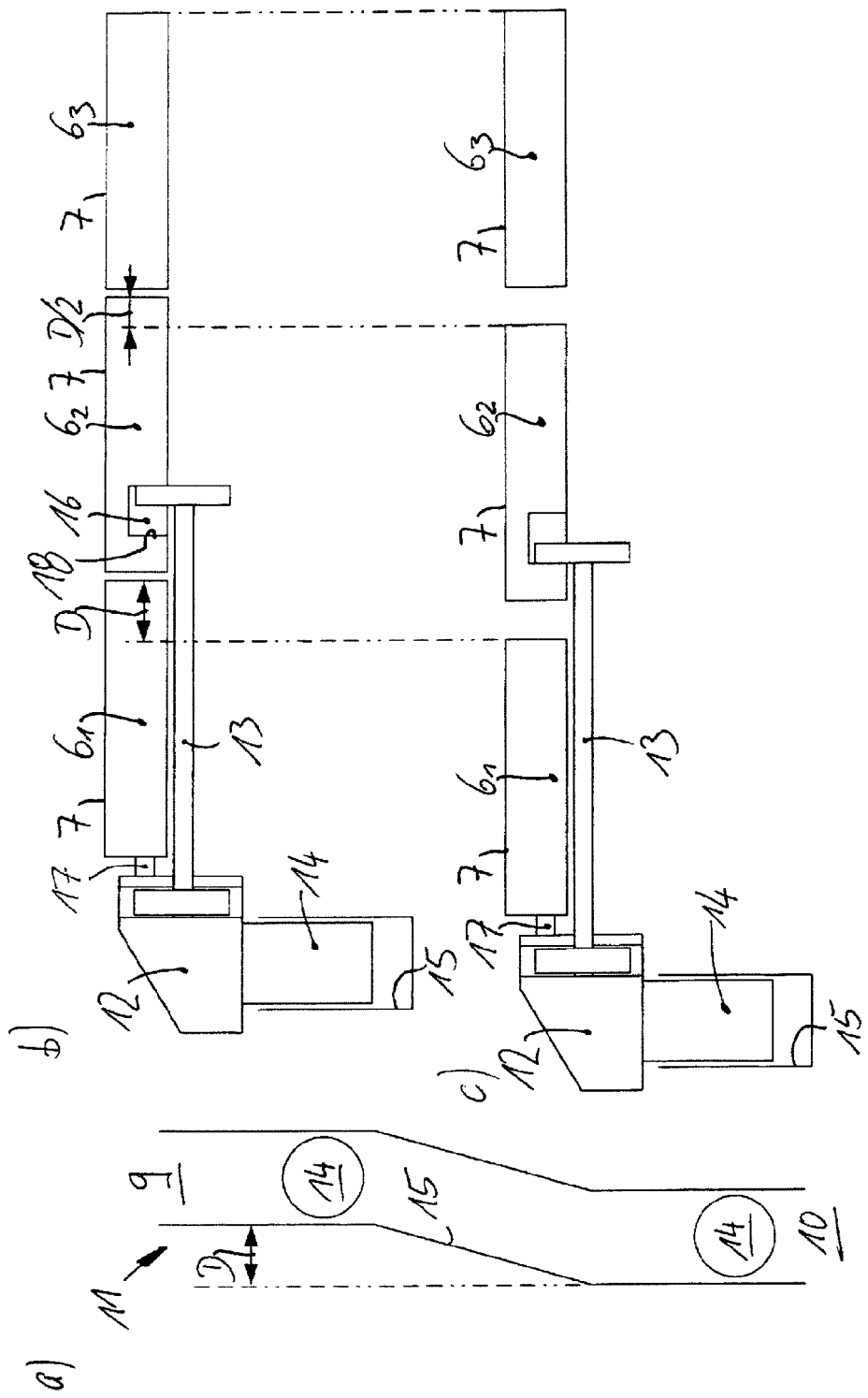

METHOD AND APPARATUS FOR SEPARATING AND STACKING SLICES OF FOOD

The invention relates to a method and a device for separating and stacking food slices, in particular cheese slices, which are continuously conveyed, adjacent to one another in rows, by an input conveyor belt and which are removed from the input conveyor belt and placed on top of one another in a stacking region by means of a rotating transfer roller.

Document EP 2 478 771 A1, which was published after the priority date, discloses a production line for the production of food. A drum, as the shaping device, shapes the product and deposits this product directly into a waiting package. Individual cavities, which are rigidly mounted on the drum, are provided for shaping the food.

A method of the type in question is described in WO 2007/122311 A1, for example. In order to stack the individual cheese slices, these are first discharged from a shaping roller onto a conveyor belt and then fall, under the force of gravity, from the conveyor belt into waiting dishes, onto the cheese slices already lying therein. The cheese slices falling into the dishes results in an uncontrollable stacking of the slices that lie on top of one another. In addition, this type of stacking is not suitable for types of cheese that are particularly soft and creamy, since the consistency of the cheese slices does not ensure sufficient shape retention.

Document DE 297 13 690 U1 also shows a device for transferring sliced food. The food slices are transported and turned on a belt. In order to provide a secure hold during the turning procedure, clamps, spikes, or the like are provided, which can damage the cheese slices, however.

The present method proceeds from a method, in which the food slices, which are cheese slices in this case, are cut from a wide product strand. After the product strand has been cut into individual strips by means of longitudinal cutting and the strips have been subsequently cut into individual slices by means of transverse cutting, the slices lie adjacent to one another in rows and are conveyed row after row on the input conveyor belt. These rows of slices adhering to one another must be separated by cutting for further processing. The separated slices can then be placed on top of one another in a stack and packaged.

Proceeding from this type of slice production, the problem is that of creating a method and a device for separating and stacking, which has an easily implemented design and ensures reliable handling and exact positioning of the food slices even if these food slices have a consistency that is particularly soft and creamy to sticky, as is the case with many cheese slices.

These problems are solved by a method according to claim 1 and a device according to claim 3. Advantageous embodiments are set forth in the particular dependent claims.

The fundamental idea of the invention is the use of the rotating transfer roller, which is disposed at the end of the input conveyor belt and which is disposed with the axis thereof at the end of the conveyor belt, transversely to the conveyor belt. This is equipped on the surface thereof with displaceable holding units, the number and arrangement of which make it possible to receive an entire incoming row of food slices, hold these food slices by means of a non-positive connection and separate these food slices from one another during rotation and, finally, place these food slices in stacks in a defined manner in the stacking region.

According to the claimed method, the transfer roller accommodates the row of food slices together by means of a plurality of holding units. The individual food slices are separated from one another in the axial direction during rotation by means of a relative movement of the holding units. Having arrived over the stacking region, the holding units release the separated cheese slices in a defined manner, thereby allowing them to be placed on top of one another ("transferred") in stacks in the stacking region. Anything that provides the stack of food slices with a supporting surface is suitable as a stacking region, such as a dish, a tray, or a plate. Preferably, however, a suitably disposed conveyor belt is the stacking region.

The non-positive connection between the slice and the holding units is advantageously implemented by means of an underpressure, which holds the food slice on the holding unit during rotation. In a corresponding manner, the separation of the held food slice can be induced by cutting off the underpressure and can be supported by generating an overpressure. The handling of the slices by means of air pressure is particularly advantageous, because this is implemented without mechanically damaging the slice and, above all, in a particularly hygienic manner. In addition, the guidance and handling of the related air flows are easy to implement.

The device according to the invention is characterized in that a plurality of holding units, which are adjacently disposed in rows, is provided on the surface of the transfer roller for holding one food slice each by means of a non-positive connection. Means are also provided for inducing an axial displacement of the holding units during rotation and, therefore, separation of the food slices adhering thereto. The holding units also comprise separating means for releasing the food slices and stacking these food slices in the stacking region, wherein the holding means and the separating means preferably utilize air pressure, as described above.

The holding units preferably provide a placement surface, which has the approximate dimensions of a food slice and onto which a slice can be placed accordingly. In particular, one separate holding unit is provided for each food slice, wherein this holding unit forms a carrier for exactly one food slice (which is also referred to in the following as a "cheese slice") during the transfer procedure. A constant force can be applied onto the cheese slices by utilizing a pressure differential, i.e. colloquially speaking by means of an underpressure or vacuum, for the non-positive retention. This makes it possible to prevent point loads, which could cause damage in the case of particularly soft and creamy cheese slices. It is nevertheless ensured that the retention on the holding unit and, therefore, the transfer roller, is reliable and that damage is prevented.

Finally, the transfer device equipped according to the invention makes it possible to transfer and exactly stack soft and creamy cheese slices. The movability of the adjacent holding units makes it possible to separate the food slices from one another, which are more or less adhering to one another. For example, cheese slices that are conveyed adjacent to one another via the input conveyor belt and that have been cut but are still attached to one another can be fed to further processing. Placed onto the holding units, the food slices are separated from one another by means of the relative movements of the holding units. To this end, adjacent holding units can be moved relative to one another in the axial direction. The food slices to be separated from one another can basically also each be disposed on a carrier foil.

The use of air underpressure to hold the cheese slices makes it possible to control the retaining force at the holding units in different ways. It can be specified in a defined manner, for example, when a food slice should be held on a holding unit and when it should be released. The release can be supported by reversing the pressure, which is particularly advantageous in the case of a sticky food product. The holding units are each provided with a placement surface for placement of the food slices, wherein the placement surfaces are provided with openings, which are connected to a pump. The connection to the pump can be controlled at least in the lower discharge region, thereby allowing the air pressure present at the openings to be switched on and off in both directions. In order to save energy, the underpressure is also switched off in the rear region, in which the holding units move back upward, empty.

Preferably, the food slices to be separated and stacked are transferred to the transfer roller in the region of a top dead center of the roller movement and the food slices being transferred are released from the transfer roller in the region of a bottom dead center of the roller movement. This has the advantage that gravity can be utilized first for the placement of the food slices, before the slice can be held via suction, wherein the slice covers all the openings. Gravity is utilized once more in the vicinity of the bottom dead center to support the release and the stacking in an exact manner. Advantageously, a pressure reversal is also implemented to detach the slice from the holding unit.

In a particular embodiment, the placement of the stacking region can be moved laterally and, preferably, in both directions of the plane. It is therefore possible to intentionally influence the shape of the developing stack by moving the stacking region in a defined manner. In particular, a fan structure can be obtained by means of a slight advancing movement, which makes it easier to subsequently simply remove individual slices from the stack by hand. The fan structure can also have a two-dimensional design if the stacking region can be moved in two directions that are oriented orthogonally relative to one another. A direction of movement in one conveyor belt direction can be implemented by an output conveyor belt, on which the stack is formed. The other displacement direction of the fan structure can be obtained by the individual slices being discharged from the transfer roller sooner or later, in a defined manner, relative to the preceding individual slice. The lateral movability in the plane is established by means of these two components of motion.

The distance between adjacent holding units is preferably dependent on the extent of rotation of the transfer roller. The distance between one holding unit and the respectively adjacent holding unit increases depending on the rotation of the transfer roller. At the transfer point at the end of the input belt, the holding units and the food slices lie close to one another, thereby allowing the food slices that are adjacent to one another to be placed next to one another on the transfer roller without gaps. As rotation occurs, separation takes place as the adjacent holding units move apart from one another. The distance therebetween stops increasing when the food slices are released from the transfer roller.

The transfer roller preferably comprises a control guide, which does not rotate along with the transfer roller. A plurality of control slides is guided along the control guide, wherein the axially movable holding units are connected in a driving manner to one of the control slides in each case. In this context, "connected in a driving manner" means that an axial movement of the control slide can induce an axial movement of the holding unit, which is connected in a driving manner, wherein this movement need not be directly transferred. In particular, a plurality of holding units disposed at a common circumferential position of the transfer roller is connected in a driving manner to a common control slide. The position of a control slide therefore influences the distance separating all axially adjacent holding units disposed at one common circumferential position. The movement of the holding units is therefore correlated to the shape of the control guide. Since the control guide does not rotate with the transfer roller, the movement of the holding units is therefore coupled to the circular movement of the holding units. Separate actuators, which control the movement of the holding units, can therefore be omitted. The connection of underpressure or overpressure to the openings of the placement surfaces can be controlled by means of this control guide or another control guide.

The drive connection between the control slide and one of the movable holding units preferably has an open path. The open path makes it possible to initially interrupt the direct coupling between the holding unit and the control slide. This means that a movement of the control slide does not yet forcibly induce a movement of the holding unit, provided the open path has not been crossed. By means of such an open path, not only can a movement of individual holding units be controlled separately, it is therefore also possible to adjust a relative movement between holding units assigned to a common control slide. In other words, the larger the open path, the smaller the movement of one holding unit. The control slide is axially movable in particular.

Furthermore, the mechanism comprising the holding units, control slides, and control rod can be removed by hand without the use of tools due to a plug-in design. To this end, the control guide has a matching recess for withdrawing the control slide. This design ensures the hygienic condition and cleanability of the transfer roller.

The invention is explained in greater detail in the following with reference to the figures, wherein FIG. 1 shows a device according to the invention for separating and stacking food slices, in a perspective view;

FIG. 2 shows details of a control arrangement for controlling the relative movement of individual holding units.

FIG. 1 shows a device 1 according to the invention for separating and stacking cheese slices 2. The cheese slices 2 are conveyed via an input conveyor belt toward a transfer roller 5. From the transfer roller 5, the cheese slices 2 are then conveyed onto an output conveyor belt 4, which is a stacking region. The transfer roller 5 is substantially cylindrical and is supported so as to be rotatable about a rotational axis A. The cheese slices 2 are placed onto the transfer roller in the region of a top dead center 9 of the roller movement. The cheese slices 2, together with the transfer roller 5, then execute a rotation about the rotational axis A by approximately 180 degrees, thereby releasing the cheese slices, which have been turned, onto the output conveyor belt 4, where they are stacked.

In order to accommodate the cheese slices 2 on the transfer roller 5, the transfer roller 5 comprises a plurality of holding plates 6, as a holding unit, which are disposed on the surface of the transfer roller 5. Each holding plate 6 is used to hold exactly one cheese slice 2. Each of the holding plates 6 has a placement surface 7 on the outwardly facing surface, on which a single cheese slice 2 is placed in each case. The placement surfaces 7 are each provided with a plurality of air openings 8 over the entire surface thereof, wherein these air openings are connected to a non-illustrated pump. In the present exemplary embodiment, only the air openings of the inner region of the holding plates are controlled with underpressure, wherein this inner region is also covered by smaller cheese slices. While the holding plate has dimensions of 100 mm×100 mm, the "vacuum region" can only cover 60 mm×60 mm. When the pump is connected, an underpressure is applied to the air openings 8. The cheese slices 2 are thereby held on the placement surface 7 via a non-positive connection. A compressed air line with overpressure can also be connected to the air openings, if necessary, in order to induce easy detachment of the cheese slices from the placement surface 7.

The holding plates 6 are movably held on the surface of the transfer roller 5. As is evident from FIG. 1, the axially adjacent holding plates 6, i.e. those that are disposed together in a horizontal row on the transfer roller 5, are held so as to be movable relative to one another. For example, the holding plates 6 in the region of the top dead center 9 are still disposed closely to one another, while the axially adjacent holding plates 6 in the region of the bottom dead center 10 are axially separated from one another. In this context it should be noted that the term "axial" is always intended to mean relative to the rotational axis A of the transfer roller 5. Although the cheese slices 2 have already been cut when they are conveyed by the input conveyor belt 3, they still lie so closely to one another that the slices are still connected to one another by individual small connecting webs. In particular when a carrier foil is used, which overlaps by 2-10 mm in the region of the longitudinally cut cheese slice, an adhesive connection of the individual slices therefore still exists. The final separation of the axially adjacent cheese slices 2 is then induced by two axially adjacent holding plates moving apart.

The mode of operation of the control of the movement of axially adjacent holding plates 6 is explained in greater detail by reference to FIG. 2. A control guide 11 having a control groove 15 is provided, the developed view of which is shown in FIG. 2a. The control guide 11 is fixedly disposed at an end face of the transfer roller 5 and therefore does not execute the rotational movement of the roller 5. The control groove 15 has a curvy course, and therefore individual regions of the control groove 15 have different axial positions relative to the rotational axis A. A control slide 12 rotates together with the transfer roller 5 and is supported at the transfer roller 5 so as to be axially movable. The control slide 12 engages in the control groove 15 via a fixedly connected control pin 14. The axial position of the control slide 12 is therefore defined depending on the shape and axial position of the control groove 15 in the region in which the control pin 14 engages in the control groove 15.

As is evident by reference to FIGS. 2b and 2c, the axial movement of the control slide 12 is now transferred to the individual holding plates 6. The control slide 12 is axially fixedly connected to the first holding plate $6_1$ via a connecting pin 17. A drive connection to the axially adjacent, second holding plate $6_2$ is obtained via a control rod 13, which is axially fixedly connected to the control slide 12. The control rod 13 is not axially fixedly connected to the second holding plate $6_2$, but rather can move partially freely in a recess 18. The recess 18 therefore provides an open path 16, along which the control rod 13 cannot move the second holding plate 6. Once the open path 16 has been crossed, the control rod 13 comes in contact with the second holding plate 6 and can axially drive the second holding plate $6_2$. The third adjacent holding plate $6_3$ is axially fixedly supported on the transfer roller 5.

If the control groove 15 now covers an axial displacement distance D, the control pin 14 and, therefore, the control slide 12 are axially displaced by the displacement distance D as this control slide moves circumferentially along the control groove 15. Due to the direct, fixed connection to the first holding plate $6_1$, the first holding plate $6_1$ is also axially displaced by the displacement distance D. The control rod 13 is also axially displaced together with the control slide 12 by the axial displacement distance D. Since the open path 16 is provided, however, the second holding plate $6_2$ is axially displaced only by the displacement distance D minus the axial open-path length (D/2 in the present case) of the open path 16. Depending on the design and the dimensioning, it is also possible, of course, to obtain other displacement distances of the second holding plate $6_2$ relative to the entire axial displacement distance D. Due to the arrangement, the individual holding plates $6_1$, $6_2$ and $6_3$ are now moved axially relative to one another, wherein the distance between the holding plates 6, relative to one another in each case, is increased by half the displacement distance D/2 in the present case. The axially adjacent cheese slices are now finally separated from one another.

FIG. 1 shows the stacking of the individual cheese slices 2 on the output conveyor belt 4. The output conveyor belt 4 is movable in the conveyor belt direction F, whereas the entire output conveyor belt 4, together with the conveyor rollers, is movable in a direction perpendicular to the conveyor belt direction F, thereby enabling individual regions of the output conveyor belt 4 to be placed in different lateral orientations relative to the transfer roller. The cheese slices 2, which will now be released from the transfer roller 5 in the region of the bottom dead center 10 by means of overpressure, can be placed onto the conveyor belt 4 at highly diverse points, depending on where this point of the conveyor belt 4 is disposed at that time due to the movability of the conveyor belt. It is possible, for example, to deposit a plurality of the cheese slices 2 that have been conveyed in succession to an axial position on a common stack. A type of fan structure can be created by slightly advancing transversely to the conveyance direction F. A type of slanted fan structure, as shown in FIG. 1, can be created by advancing in a direction transversely to the conveyance direction F and longitudinally relative to the conveyance direction F. The movability of the output conveyor belt 4 in both directions orthogonally relative to one another makes it possible to create a plurality of stacking patterns.

LIST OF REFERENCE SIGNS 1 device for separating and stacking
2 cheese slices
3 input conveyor belt
4 output conveyor belt
5 transfer roller
6 holding plate
7 placement surface
8 air opening
9 top dead center
10 bottom dead center
11 control guide
12 control slide
13 control rod
14 control pin
15 control groove
16 open path
17 connecting pin
18 recess
F conveyor belt direction
A rotational axis
D displacement distance

The invention claimed is:

1. A device (1) for separating and stacking food slices in a stacking region (4) comprising:
   an input conveyor belt (3) having a direction of conveyance (F) for continuously conveying food slices (2) disposed adjacent to one another in rows (2),
   a rotatable transfer roller (5) having a rotational axis transversely disposed relative to the direction of conveyance (F) of the input conveyor belt (3) located proximal to the end of the input conveyor belt (3),
   a stacking region (4) below and proximal to the transfer roller (5) for placing food slices (2) on top of one another in stacks,
   wherein
   a plurality of holding units (6) disposed laterally adjacent to one another in rows is provided on the surface of the transfer roller (5) suitable for holding one food slice (2) each, wherein the transfer roller (5) comprises a control guide (11) and a plurality of axially-oriented control slides (12) guided at the control guide (11) for defining the axial position of the control slides, wherein each control slide (12) is engagable in a drivable manner with at least one holding unit (6), wherein the control guide (11) and the plurality of axially-oriented control slides (12) are adapted to induce axial displacement of the holding units away from each other during rotation from a position above the rotational axis of the rotatable transfer roller (5) to a position below the rotational axis of the rotatable transfer roller (5) and
   the control slide (12) is connected to at least one holding unit (6) via a drive connection between the control slide (12) and at least one of the movable holding units ($6_2$), wherein the drive connection comprises an open path (16) for allowing axial displacement of the control slide (12) for a given distance independent from the axial position of the holding unit (6) having the drive connection with the open path (16).

2. The device (1) according to claim 1, wherein the holding units (6) comprise a placement surface (7) having openings (8), wherein air can be withdrawn via the openings (8) to apply a vacuum and/or air can be supplied via the openings (8) to apply air pressure.

3. The device (1) according to claim 1, wherein the stacking region (4) is laterally movable relative to the input conveyor belt direction (F).

4. The device (1) according to claim 1, wherein the stacking region is formed by an output conveyor belt (4) movable transversely to the input conveyor belt direction (F) thereof.

5. The device (1) according to claim 1, wherein the control guide (11) comprises a control groove (15) and each control slide (12) is engaged in a drivable manner with the control groove (15) for controlling the distance between adjacent holding units (6) relative to the rotational position of each control slide (12) during rotation of the transfer roller (5).

6. The device (1) according to claim 1, wherein a plurality of holding units (6) disposed at a common circumferential position of the transfer roller (5) are engagable in a drivable manner with a common control slide.

7. The device (1) according to claim 1, wherein the control slide (12) is connected to multiple holding units (6) via a drive connection between the control slide (12) and the multiple movable holding units (6), wherein the drive connection comprises an open path (16) for allowing axial displacement of the control slide (12) for a given distance independent from the axial position of more than one of the multiple holding units (6) having the drive connection with the open path (16).

8. A method for separating and stacking food slices (2) comprising:
   conveying a plurality of food slices (2) in a conveyance direction toward a transfer roller (5) rotating about an axis of rotation, wherein the food slices (2) are arranged in rows transverse to the conveyance direction,
   transferring each row of conveyed food slices (2) to the rotating transfer roller (5) above the axis of rotation,
   applying a vacuum to each food slice (2) transferred to the rotating transfer roller (5) to hold each food slice on the rotating transfer roller (5),
   sequentially displacing the food slices (2) in each transferred row of food slices (2) held on the rotating transfer roller (5) away from each other parallel to the axis of rotation while rotating each row of food slices (2) from a position above the axis of rotation of the transfer roller (5) to a position below the axis of rotation of the transfer roller (5), wherein each transferred row of food slices (2) comprises at least a first slice (2), a second slice (2) adjacent to the first slice (2) and a third slice (2) adjacent to the second slice (2), wherein displacement of the third slice (2) parallel to the axial direction is initiated after initiating displacement of the second slice (2) parallel to the axial direction in the same direction as displacement of the third slice (2) and displacement of the second slice (2) parallel to the axial direction is initiated after initiating displacement of the first slice (2) parallel to the axial direction in the same direction as displacement of the second slice (2) and
   transferring the displaced food slices (2) from the rotating transfer roller (5) to a stacking region (4) below the axis of rotation of the rotating transfer roller (5) by releasing the vacuum holding each food slice (2) as each food slice (2) is rotated into a position above and proximal to the stacking region (4) such that the food slices are placed on top of one another in stacks in the stacking region (4) to form individual stacks in the stacking region that are spaced apart from each other,
   wherein the method is carried out in accordance with the functionality of the device according to claim 1.

9. The method according to claim 8, wherein the food slices (2) are held on the rotating transfer roller (5) by holding units (6) mounted on the rotating transfer roller (5), wherein the holding units (6) are arranged in rows transverse to the conveyance direction, such that each row of holding units (6) receives one row of food slices (2) during transferring each row of food slices (2) to the rotating transfer roller (5), wherein each holding unit (6) applies a vacuum to the interface between each holding unit (6) and each food slice (2) during rotation of the transfer roller (5),
   the displacement of the food slices (2) away from each other is carried out by displacing the holding units (6) away from each other parallel to the axis of rotation while rotating the transfer roller (5) and
   the transfer of the displaced food slices (2) to the stacking region region (4) comprises releasing the vacuum at the interface between each holding unit (6) and the food slice (2).

* * * * *